US00PP22375P2

(12) United States Plant Patent
van Haaster

(10) Patent No.: US PP22,375 P2
(45) Date of Patent: Dec. 20, 2011

(54) ***DAHLIA* PLANT NAMED 'FIDAHHYPDANIGHT'**

(50) Latin Name: *Dahlia variabilis*
Varietal Denomination: Fidahhypdanight

(75) Inventor: Johanna G. H. van Haaster, Hillegom (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/806,254

(22) Filed: Aug. 7, 2010

(51) Int. Cl.
*A01H 5/00* (2006.01)

(52) U.S. Cl. ..... Plt./321

(58) Field of Classification Search ..... Plt./321
See application file for complete search history.

*Primary Examiner* — Susan McCormick Ewoldt
(74) *Attorney, Agent, or Firm* — C. A. Whealy

(57) ABSTRACT

A new and distinct cultivar of *Dahlia* plant named 'Fidahhypdanight', characterized by its upright, somewhat outwardly spreading and mounded plant habit; early and freely flowering habit; large inflorescences with dark purple-colored ray florets; and good postproduction longevity.

2 Drawing Sheets

Botanical designation: *Dahlia variabilis.*
Cultivar denomination: 'FIDAHHYPDANIGHT'.

BACKGROUND OF THE INVENTION

The present invention relates to a new and distinct cultivar of *Dahlia* plant, botanically known as *Dahlia variabilis*, and hereinafter referred to by the name 'Fidahhypdanight'.

The new *Dahlia* plant is a product of a planned breeding program conducted by the Inventor in Hillegom, The Netherlands. The objective of the breeding program is to create new pot-type *Dahlia* cultivars that have a freely branching and flowering habit, attractive ray floret coloration and good postproduction longevity.

The new *Dahlia* plant originated from an open-pollination in Hillegom, The Netherlands of an unnamed selection of *Dahlia variabilis*, not patented, as the female, or seed, parent with an unknown selection of *Dahlia variabilis* as the male, or pollen, parent. The new *Dahlia* was discovered and selected by the Inventor as a single flowering plant from within the progeny of the stated open-pollination in a controlled environment in Hillegom, The Netherlands.

Asexual reproduction of the new *Dahlia* plant by cuttings in a controlled environment in Hillegom, The Netherlands since 2007, has shown that the unique features of this new *Dahlia* plant are stable and reproduced true to type in successive generations.

SUMMARY OF THE INVENTION

Plants of the new *Dahlia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Fidahhypdanight'. These characteristics in combination distinguish 'Fidahhypdanight' as a new and distinct cultivar of *Dahlia* plant:

1. Upright, somewhat outwardly spreading and mounded plant habit.

2. Early and freely flowering habit.
3. Large inflorescences with dark purple-colored ray florets.
4. Good postproduction longevity.

Compared to plants of the female parent selection, plants of the new *Dahlia* differ primarily in ray floret coloration and plant shape.

Plants of the new *Dahlia* can be compared to plants of *Dahlia* 'Fidahhypor', not patented. In side-by-side comparisons conducted in De Lier, The Netherlands, plants of the new *Dahlia* differed from plants of 'Fidahhypor' in the following characteristics:

1. Plants of the new *Dahlia* were not as freely branching as plants of 'Fidahhypor'.
2. Plants of the new *Dahlia* had longer peduncles than plants of 'Fidahhypor'.
3. Plants of the new *Dahlia* and 'Fidahhypor' differed in ray floret color as plants of 'Fidahhypor' had orange-colored ray florets.

BRIEF DESCRIPTION OF THE PHOTOGRAPHS

The accompanying photographs illustrate the overall appearance of the new *Dahlia* plant. The photographs show the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'Fidahhypdanight' grown in a container.

The photograph on the second sheet is a close-up view of a typical inflorescence of 'Fidahhypdanight'.

DETAILED BOTANICAL DESCRIPTION

The aforementioned photographs and the following observations and measurements describe plants grown during the winter in 15-cm containers in a glass-covered greenhouse in De Lier, The Netherlands under conditions and practices which approximate those generally used in commercial

*Dahlia* production. During the production of the plants, day and night temperatures averaged 18° C. Plants were eight weeks old when the photographs and description were taken. In the following description, color references are made to The Royal Horticultural Society Colour Chart, Fifth Edition, except where general terms of ordinary dictionary significance are used.

Botanical classification: *Dahlia variabilis* 'Fidahhypdanight'.

Parentage:

*Female, or seed, parent.*—Unnamed selection of *Dahlia variabilis*, not patented.

*Male, or pollen, parent.*—Unknown selection of *Dahlia variabilis*, not patented.

Propagation:

*Type.*—By cuttings.

*Time to initiate roots, summer.*—About six days at temperatures of about 22° C.

*Time to initiate roots, winter.*—About eight days at temperatures of about 20° C.

*Time to produce a rooted young plant, summer.*—About 12 days at temperatures of about 22° C.

*Time to produce a rooted young plant, winter.*—About 16 days at temperatures of about 20° C.

*Root description.*—Fine, fibrous; tuber development has not been observed.

*Rooting habit.*—Freely branching; dense.

Plant description:

*Plant form/growth habit.*—Upright, somewhat outwardly spreading and mounded plant form; broad inverted triangle; three primary lateral branches develop each primary lateral branch with numerous secondary branches; inflorescences held above the foliage on strong peduncles; bushy and dense habit; moderately vigorous growth habit.

*Plant height.*—About 28 cm.

*Plant diameter or spread.*—About 34 cm.

*Lateral branches.*—Length: About 23 cm. Diameter: About 7 mm. Internode length: About 1.5 cm to 2.5 cm. Aspect: Erect to somewhat outwardly spreading. Strength: Moderately strong. Texture: Smooth, glabrous. Color: Close to 144B tinged with close to 178A.

Foliage description:

*Arrangement.*—Leaves opposite; leaves may be single or compound with three or five leaflets.

*Shape.*—Ovate.

*Apex.*—Acute.

*Base.*—Attenuate.

*Margin.*—Serrate to dentate.

*Leaf length.*—About 14 cm.

*Leaf width.*—About 8 cm.

*Venation pattern.*—Pinnate.

*Texture, upper and lower surfaces.*—Slightly pubescent.

*Color.*—Developing leaves, upper surface: Close to 137A. Developing leaves, lower surface: Close to 138B. Fully expanded leaves, upper surface: Close to N137B; venation, close to 138B. Fully expanded leaves, lower surface: Close to 138B; venation, close to 138B.

*Petioles.*—Length: About 3.8 cm. Diameter: About 5 mm. Texture, upper and lower surfaces: Smooth, glabrous. Color, upper and lower surfaces: Close to 138B tinted with close to 178B.

Inflorescence description:

*Appearance and arrangement.*—Rotate inflorescence form with ray florets forming acropetally on a receptacle; inflorescences positioned above the foliage on strong peduncles; inflorescences face upright to outwardly; freely flowering habit, about 20 inflorescences develop per plant.

*Fragrance.*—None detected.

*Time to flower.*—Plants flower continuously from spring through the autumn in The Netherlands; early flowering habit, plants begin flowering about seven to eight weeks after planting.

*Post-production longevity.*—Inflorescences maintain good substance for about two weeks on the plant; inflorescences persistent.

*Inflorescence bud.*—Height: About 6 mm. Diameter: About 6 mm. Shape: Globular, flattened. Color: Close to 144C.

*Inflorescence size.*—Diameter: About 8 cm. Depth (height): About 2.5 cm. Disc diameter: About 5 mm. Receptacle height: About 1.8 cm. Receptacle diameter: About 3 cm.

*Ray florets.*—Length: About 3.7 cm. Width: About 1.8 cm. Shape: Oblanceolate. Apex: Obtuse; praemorse. Base: Cuneate. Margin: Entire. Aspect: Initially upright to eventually roughly perpendicular to the peduncle; florets cupped. Texture, upper and lower surfaces: Smooth, glabrous. Color: When opening, upper surface: Close to 187A. When opening, lower surface: Close to 187A to 187B. Fully opened, upper surface: Close to 53A; color does not fade with development. Fully opened, lower surface: Close to 187B to 187D; color does not fade with development.

*Disc florets.*—Length: About 1.3 cm. Diameter: At the apex, about 3 mm; at the base, about 1 mm. Shape: Tubular, elongated; apices obtuse. Number of disc florets per inflorescence: About 16. Color, when opening: Apex and mid-section: Close to 17A. Base: Close to 1B. Color, fully opened: Apex: Close to 17A. Mid-section: Close to 5B. Base: Close to 4D.

*Phyllaries.*—Quantity per inflorescence: About six arranged in a single whorl. Length: About 1.8 cm. Width: About 6 mm. Shape: Ovate. Apex: Acute. Base: Cuneate. Margin: Entire. Texture, upper and lower surfaces: Smooth, glabrous. Color, upper surface: Close to 137B. Color, lower surface: Close to 143A.

*Peduncles.*—Length: About 12 cm. Diameter: About 4 mm. Aspect: Mostly erect. Strength: Strong. Texture: Smooth, glabrous. Color: Close to 144B tinted with close to 178B.

*Reproductive organs.*—Androecium: Quantity per floret: About ten. Filament length: About 1 mm. Filament color: Close to 17A. Anther shape: Narrowly elliptic. Anther length: About 2 mm. Anther color: Close to 17A. Pollen amount: Moderate. Pollen color: Close to 25A. Gynoecium: Not observed. Seeds/fruits: Seed and fruit development have not been observed.

Disease/pest resistance: Plants of the new *Dahlia* have not been shown to be resistant to pathogens and pests common to *Dahlia*.

Garden performance: Plants of the new *Dahlia* have exhibited good tolerance to rain and wind, to tolerate high temperatures of about 35° C.; and hardy to USDA Hardiness Zone 8.

It is claimed:

1. A new and distinct *Dahlia* plant named 'Fidahhypdanight' as illustrated and described.

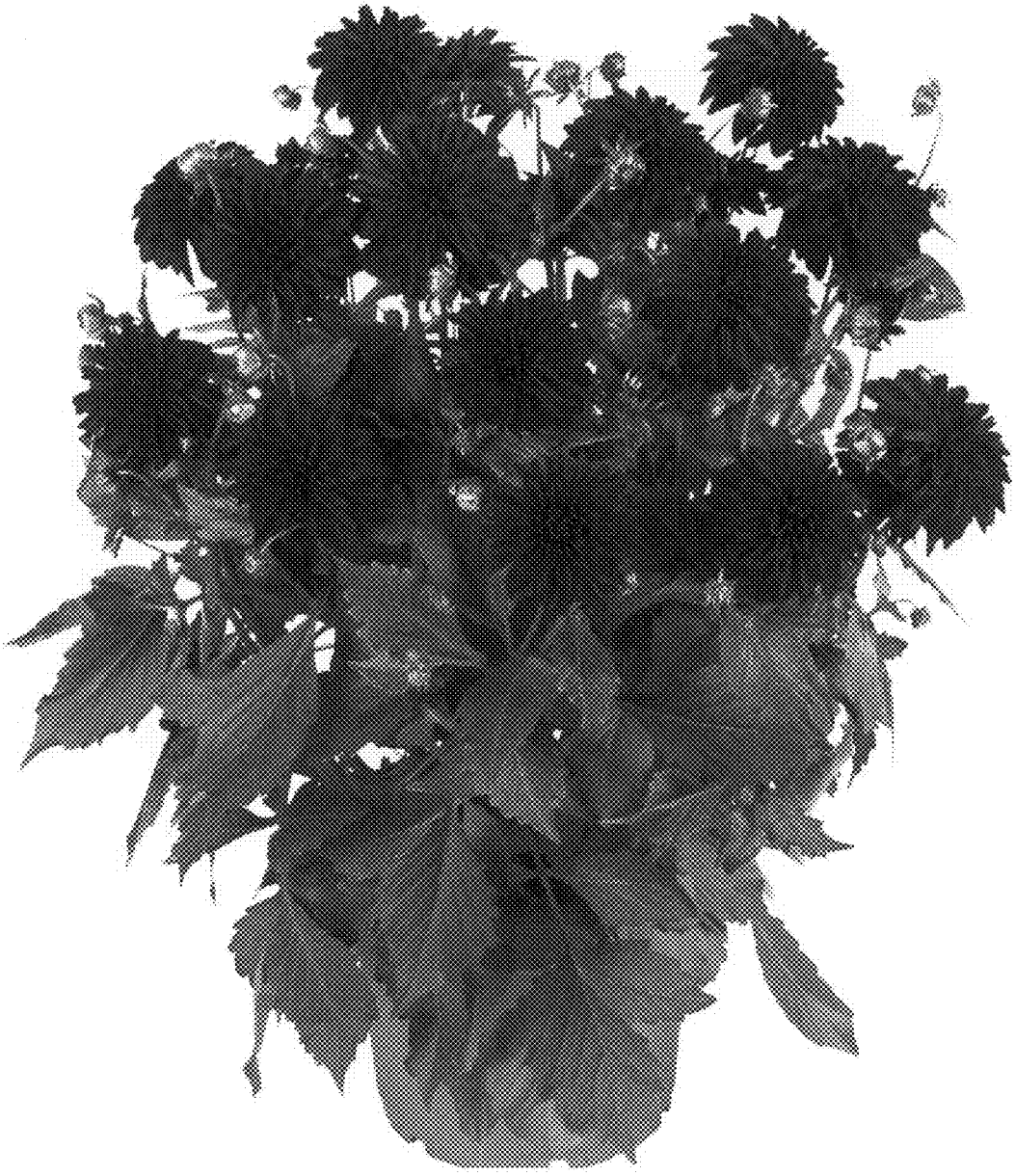

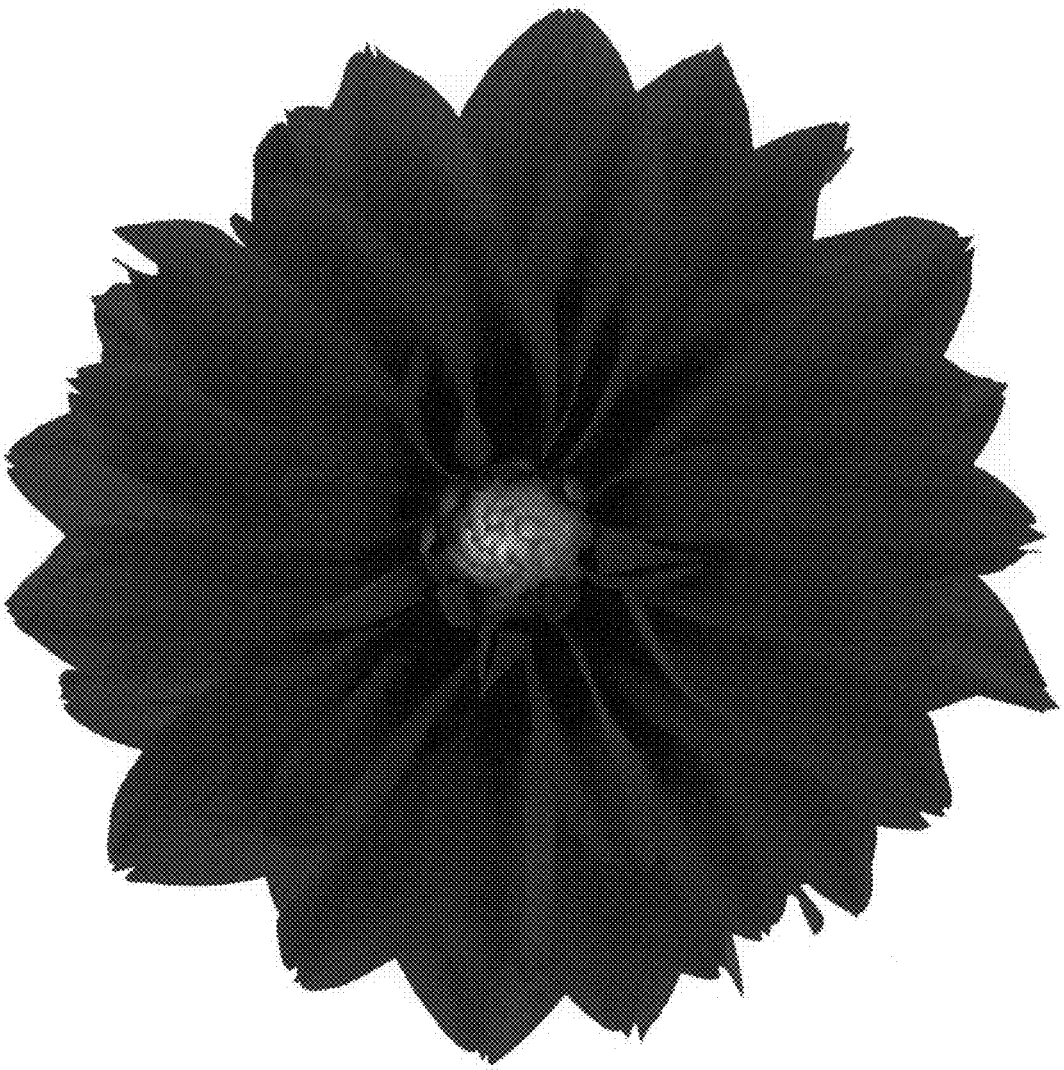

* * * * *